(12) United States Patent
Kajiki et al.

(10) Patent No.: US 8,514,399 B2
(45) Date of Patent: Aug. 20, 2013

(54) COMPENSATION IN TERAHERTZ TIME DOMAIN SPECTROSCOPY HAVING TWO DELAYS

(75) Inventors: Kousuke Kajiki, Tokyo (JP); Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 485 days.

(21) Appl. No.: 12/364,422

(22) Filed: Feb. 2, 2009

(65) Prior Publication Data
US 2009/0198466 A1    Aug. 6, 2009

(30) Foreign Application Priority Data

Feb. 5, 2008    (JP) .................................. 2008-024631
Dec. 19, 2008    (JP) .................................. 2008-324791

(51) Int. Cl.
*G01J 5/02*    (2006.01)
*G01J 3/45*    (2006.01)

(52) U.S. Cl.
USPC ........................................ 356/451; 250/341.5

(58) Field of Classification Search
USPC ................. 250/338.1, 339.01–339.14, 341.8, 250/341.5, 341.1; 356/450, 451
See application file for complete search history.

(56) References Cited

U.S. PATENT DOCUMENTS

| 7,507,966 | B2 * | 3/2009 | Nishizawa et al. | ....... 250/339.07 |
| 7,551,269 | B2 * | 6/2009 | Itsuji | ................................ 356/51 |
| 7,557,588 | B2 | 7/2009 | Ouchi et al. | ................... 324/637 |
| 7,564,034 | B2 | 7/2009 | Ouchi | ........................... 250/340 |
| 7,663,107 | B2 * | 2/2010 | Taday | ..................... 250/339.11 |
| 7,705,311 | B2 * | 4/2010 | Nishizawa et al. | ....... 250/339.07 |
| 7,781,737 | B2 * | 8/2010 | Zhdaneev | ............... 250/339.08 |
| 2006/0085160 | A1 | 4/2006 | Ouchi | .......................... 702/150 |
| 2006/0227340 | A1 | 10/2006 | Shioda et al. | .................. 356/614 |
| 2006/0237650 | A1 | 10/2006 | Taday | ...................... 250/339.11 |
| 2007/0195921 | A1 | 8/2007 | Ouchi | ............................. 378/1 |
| 2007/0229094 | A1 | 10/2007 | Kasai et al. | ................... 324/639 |
| 2007/0257216 | A1 * | 11/2007 | Withers et al. | ............... 250/580 |
| 2008/0304038 | A1 | 12/2008 | Ouchi | .............................. 356/3 |
| 2008/0314152 | A1 | 12/2008 | Ouchi | ............................ 73/597 |
| 2009/0056455 | A1 | 3/2009 | Ouchi | ............................ 73/643 |
| 2009/0201030 | A1 | 8/2009 | Ouchi et al. | ................... 324/637 |
| 2009/0213880 | A1 | 8/2009 | Ouchi et al. | ..................... 372/21 |
| 2010/0308223 | A1 * | 12/2010 | Itsuji | ............................ 250/340 |

FOREIGN PATENT DOCUMENTS

JP    2006-526774    11/2006

* cited by examiner

*Primary Examiner* — Hwa Lee
(74) *Attorney, Agent, or Firm* — Fitzpatrick, Cella, Harper & Scinto

(57) ABSTRACT

An information acquiring apparatus includes a light source portion for generating pulse-shaped pump light, and first and second probe light in synchronization with each other. A generating portion generates terahertz pulses when irradiated with the pump light. A detecting portion detects pulses of terahertz radiation from the object. A first delay portion adjusts an optical path difference between optical paths of the pump light and the first probe light reaching the detecting portion, so that the detecting portion detects a field intensity of a fixed point on the time domain waveform of the terahertz pulse from the object, following the fixed point. A second delay portion adjusts an optical path difference between the optical path of the pump light and the second probe light reaching the detecting portion by a sum of an additional optical path adjustment amount and the optical path difference, so that the detecting portion obtains the time domain waveform. A correction processing portion compensates for influence of a change in condition of the object on the time domain waveform, using the field intensity of the fixed point, or the adjustment amount adjusted by the first delay portion.

3 Claims, 18 Drawing Sheets

COMPENSATION IN TERAHERTZ TIME DOMAIN SPECTROSCOPY HAVING TWO DELAYS

BACKGROUND OF THE INVENTION

1. Field of the Invention

The present invention relates to information acquiring apparatuses and methods for obtaining information, such as characteristics, of an object by using electromagnetic radiation. More particularly, the present invention relates to information acquiring apparatuses and methods for obtaining information of an object by using terahertz (THz) radiation.

2. Description of the Related Background Art

In this specification, the terminology "terahertz (THz) radiation", or the like is used for electromagnetic radiation containing a radiation component in a frequency range between about 30 GHz and about 30 THz. In recent years, non-destructive sensing technology using terahertz radiation has been developed and searched. Technical fields using such terahertz radiation include imaging fields using safe see-through examining apparatuses in place of X-ray apparatuses.

Further, development has also been made with respect to spectroscopic technology for acquiring absorption spectra and complex dielectric constants to examine characteristics, such as bonding condition, of substances, analytic technology for analyzing bio-molecules, estimating technology for estimating carrier concentration and mobility, and the like. An example of application of the above technology includes an apparatus of examining a component or particle size of medicine in a medicine producing process. It is desired to develop an examining apparatus utilizing features of terahertz radiation and capable of non-destructive in-process measurement.

A typical spectroscopic analyzing method using terahertz radiation includes the terahertz time domain spectroscopy (THz-TDS). The THz-TDS is capable of measuring the time domain waveform of electric field intensity of a terahertz pulse. JP 2006-526774 A (corresponding to US2006237650) discloses technology of Fourier-transforming the time domain waveform to acquire its spectrum, and identifying component of an object by an analyzing method using calibration curves or the like.

When a component or particle size of an object is measured in an in-process manner during a step of transporting, supplying and mixing objects such as powder and particles, the thickness or density of the object may change within a time shorter than a time for acquiring the time domain waveform of terahertz pulse. However, the technology described in JP 2006-526774 A is not seen to consider such a change in thickness and density. Accordingly, there is a possibility that a component of the change is superimposed on the time domain waveform of measured terahertz pulse. Therefore, it is not easy to improve the analytic precision of information, such as component or particle size, of the object.

SUMMARY OF THE INVENTION

It is an object of the present invention to provide apparatuses and methods for obtaining information of an object by using electromagnetic radiation.

According to one aspect of the present invention, there is provided an information acquiring apparatus for acquiring information of an object by using terahertz time domain spectroscopy, which includes a light source portion, a generating portion, a detecting portion, a first delay portion, a second delay portion, and a correction processing portion. The light source portion is configured to generate pulse-shaped pump light, first probe light and second probe light in synchronization with each other. The generating portion is configured to generate pulses of terahertz radiation by irradiation with the pump light. The detecting portion is configured to detect pulses of terahertz radiation from the object irradiated with the pulses of terahertz radiation from the generating portion.

The first delay portion is configured to adjust an optical path difference between an optical path of the pump light reaching the generating portion and an optical path of the first probe light reaching the detecting portion, so that the detecting portion detects a field intensity of a predetermined fixed point on a time domain waveform of the pulse of terahertz radiation from the object, following the predetermined fixed point. The second delay portion is configured to adjust an optical path difference between the optical path of the pump light reaching the generating portion and an optical path of the second probe light reaching the detecting portion by a sum of an additional optical path adjustment amount and the optical path difference adjusted by the first delay portion, so that the detecting portion obtains the time domain waveform of the pulse of terahertz radiation from the object. The correction processing portion is configured to compensate for influence of a change in condition of the object on the time domain waveform obtained by the detecting portion, using the field intensity of the predetermined fixed point, or an adjustment amount of the optical path adjusted by the first delay portion.

According to another aspect of the present invention, there is provided an information acquiring method for acquiring information of an object by using terahertz time domain spectroscopy, which includes a first generating step, a second generating step, a detecting step, a first delay step, a second delay step, and a correction processing step. In the first generating step, generating pulse-shaped pump light, first probe light and second probe light are generated in synchronization with each other. In the second generating step, pulses of terahertz radiation are generated by using the pump light. In the detecting step, pulses of terahertz radiation from an object irradiated with the pulses of terahertz radiation are detected.

In the first delay step, an optical path difference between an optical path of the pump light used in the second generating step and an optical path of the first probe light used in the detecting step is adjusted, so that a field intensity of a predetermined fixed point on a time domain waveform of the pulse of terahertz radiation from the object is detected in the detecting step, following the predetermined fixed point. In the second delay step, an optical path difference between the optical path of the pump light used in the second generating step and an optical path of the second probe light used in the detecting step is adjusted by a sum of an additional optical path adjustment amount and the optical path difference adjusted in the first delay step, so that the time domain waveform of the pulse of terahertz radiation from the object is obtained in the detecting step. In the correction processing step, influence of a change in condition of the object on the time domain waveform obtained in the detecting step is compensated for by using the field intensity of the predetermined fixed point, or an adjustment amount of the optical path adjusted in the first delay step.

According to yet another aspect of the present invention, there is provided an information acquiring method for acquiring information of an object, which includes a light source portion, a generating portion, a detecting portion, a first delay portion, a fixed-point adjusting portion, a second delay portion, and a correction processing portion. The light source portion is configured to generate pulse-shaped pump light, first probe light and second probe light in such a manner that repetitive frequencies of the pump light, the first probe light and the second probe light are coincident with each other. The generating portion is configured to generate pulses of terahertz radiation by irradiation with the pump light. The detecting portion is configured to detect a field intensity of the pulse of terahertz radiation transmitted through or reflected by the object by irradiation with the first probe light and the second probe light.

The first delay portion is configured to change a first optical path difference between an optical path of the pump light from the light source portion to the generating portion and an optical path of the first probe light from the light source portion to the detecting portion. The fixed-point adjusting portion is configured to control the first delay portion so that a predetermined fixed point set on a time domain waveform of the pulse of terahertz radiation transmitted through or reflected by the object is followed. The second delay portion is configured to change a second optical path difference between the optical path of the pump light from the light source portion to the generating portion and an optical path of the second probe light from the light source portion to the detecting portion. The correction processing portion is configured to adjust the second optical path difference by addition of the first optical path difference adjusted by the control of the first delay portion with the fixed-point adjusting portion. The time domain waveform of the pulse of terahertz radiation transmitted through or reflected by the object is corrected by the correction processing portion, and acquired.

According to yet another aspect of the present invention, there is provided an apparatus for acquiring a time domain waveform of terahertz radiation, which includes a generating portion, a detecting portion, first and second delay portions, a first control portion, and a second control portion. The generating portion is configured to generate terahertz radiation. The detecting portion is configured to detect intensity information of the terahertz radiation. The first and second delay portions are configured to change times at which the terahertz radiation is detected by the detecting portion, respectively. The first control portion is configured to control the first delay portion so that predetermined change information of the intensity information of the terahertz radiation detected by the detecting portion is obtained. The second control portion is configured to control the second delay portion so that a time domain waveform of the terahertz radiation is acquired. The time domain waveform is acquired based on the control of the first delay portion by the first control portion.

According to the apparatuses and methods of the present invention, using the above-described correction processing portion or the correction processing step, influence of a change in condition, such as thickness or density, of the object on the time domain waveform of terahertz pulse from the object is compensated for. Accordingly, the above influence can be reduced in measuring the time domain waveform of terahertz pulse from the object. Therefore, it is possible to improve the analytic precision of information, such as component or particle size, of the object acquired by using the terahertz time domain spectroscopy.

Further features of the present invention will become apparent from the following description of exemplary embodiments with reference to the attached drawings.

DESCRIPTION OF THE EMBODIMENTS

Figure 1:
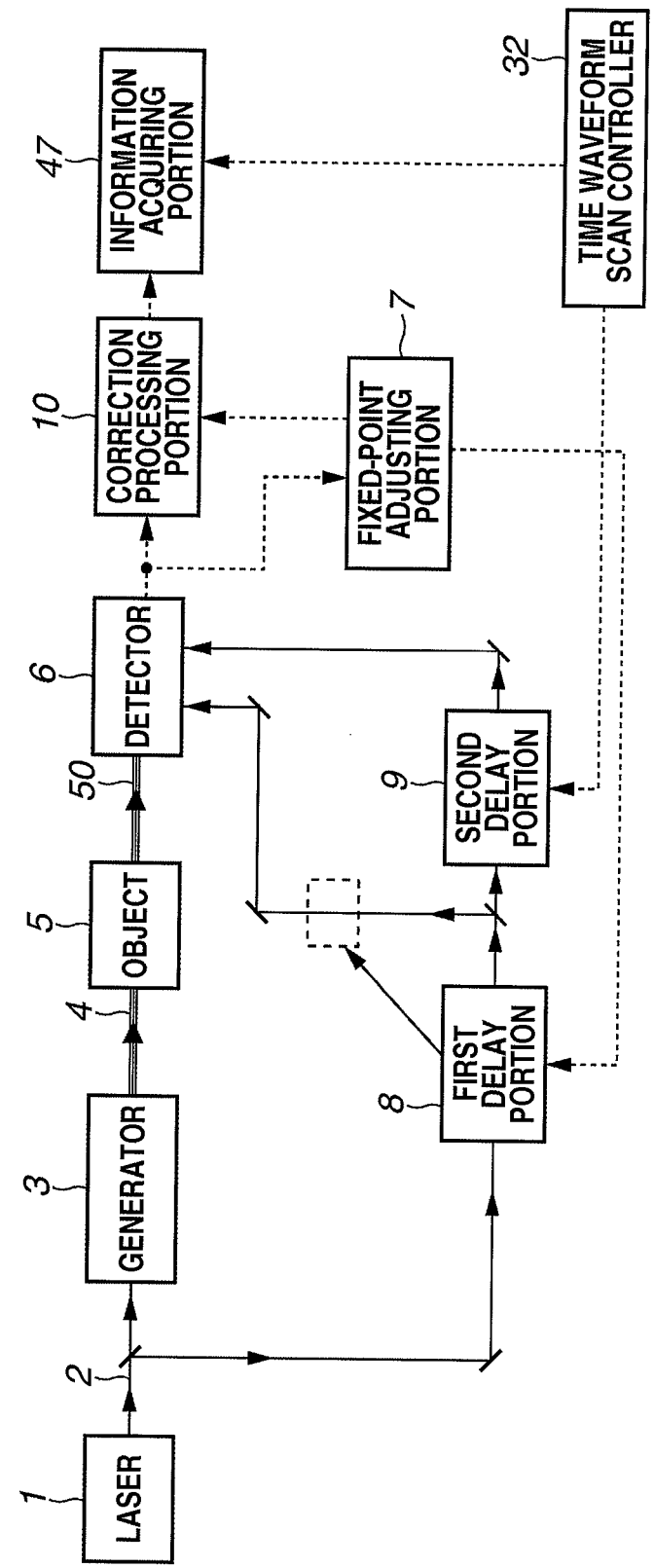
FIG. 1 is a view illustrating an example embodiment of an information acquiring apparatus and method according to the present invention.

Principles of the present invention and embodiments of the present invention will now be described.

An information acquiring apparatus and method of the present invention includes the following elements or steps for achieving the above-described technical advantage. In the apparatus and method, the time domain waveform of terahertz radiation is acquired, and information of the object is obtained, using the terahertz time domain spectroscopy (THz-TDS).

A light source portion generates pump light, first probe light and second probe light, for example, in the form of pulse-shaped laser light, in synchronization with each other (typically, so that repetitive frequencies of these light are coincident with each other).

A generating portion for generating terahertz radiation emits terahertz pulses when a device, such as a photoconductive device, is irradiated with pulse-shaped pump light. A detecting portion for detecting intensity information (or field intensity) of terahertz radiation detects terahertz pulses that are reflected by or transmitted through the object irradiated with terahertz pulses from the generating portion, when a device, such as a photoconductive device, is irradiated with the pulse-shaped probe light.

A first delay portion for changing detection time of the terahertz radiation by the detecting portion adjusts an optical path difference between an optical path of the pump light reaching the generating portion and an optical path of the pulse-shaped first probe light reaching the detecting portion, so that a predetermined fixed point on the time domain waveform of the terahertz pulse from the object can be followed and the field intensity thereof can be detected. Alternatively, a fixed-point following portion is provided to control the first delay portion so that a predetermined fixed point on the time domain waveform of the terahertz pulse from the object can be followed.

A second delay portion adjusts an optical path difference between the optical path of the above-stated pump light and an optical path of pulse-shaped second probe light reaching the detecting portion, by adding an additional adjustment amount of the optical path to the optical path difference adjusted with the first delay portion, so that the time domain waveform can be obtained by the detecting portion.

A correction processing portion compensates for influence of a change in condition of the object on the time domain waveform by using the field intensity of the above predetermined fixed point, or the adjustment amount of the optical path by the first delay portion.

It is helpful to provide a first controller for controlling the first delay portion, so that predetermined change information of intensity information of the terahertz radiation detected by the detecting portion can be acquired. It is further helpful to provide a second controller for controlling the second delay portion, so that the time domain waveform of the terahertz radiation can be acquired. The above-described technical advantage can be obtained when the time domain waveform is acquired by the control of the first delay portion with the first controller. Thus, it is possible to compensate for the influence of a change in condition, such as thickness or density, of the object on the time domain waveform of the terahertz pulse from the object.

The influence is deviation of, for example, a peak position (a fixed point) on the time domain waveform of the terahertz pulse from the object. When the second delay portion is controlled based on the amount of the deviation, a corrected time domain waveform can be acquired.

In a method of acquiring information of an object using the terahertz time-domain spectroscopy, pulse-shaped pump light, first probe light and second probe light are generated in synchronization with each other in a first generating step. In a second generating step, terahertz pulses are generated by irradiation of a device, such as a photoconductive device, with pulse-shaped pump light. In a detecting step, terahertz pulses from the object are detected by irradiating a device, such as a photoconductive device, with the above pulse-shaped probe light.

In a first delay step, an optical path difference between an optical path of the pump light in the second generating step and an optical path of the pulse-shaped first probe light in the detecting step is adjusted, so that a predetermined fixed point on the time domain waveform of the terahertz pulse from the object can be followed and the field intensity thereof can be detected in the detecting step.

In a second delay step, an optical path difference between the optical path of the above pump light in the second generating step and an optical path of pulse-shaped second probe light in the detecting step is adjusted, by adding an additional adjustment amount of the optical path to the optical path difference adjusted in the first delay step, so that the time domain waveform can be obtained in the detecting step.

In a correction processing step, influence of a change in condition of the object on the above time domain waveform is compensated for by using the field intensity of the predetermined fixed point, or the adjustment amount of the optical path in the first delay step.

In terms of time, the above optical path difference is a relative delay time between the pump light and the probe light obtained by dividing the optical path difference by the velocity of light. Further, the above predetermined fixed point includes at least a point, such as a point of an extreme value, and is, for example, a peak point of the time domain waveform of the terahertz pulse from the object.

In the above-discussed construction, influence of a change in condition, such as thickness or density of the object, on the time domain waveform is compensated for by the correction processing portion, or in the correction processing step. Accordingly, precision of information of the object acquired by using the terahertz time domain spectroscopy can be improved. Thus, information of the object disposed between the generating portion and the detecting portion can be precisely obtained from the time domain waveform of the terahertz pulse from the object.

To obtain the time domain waveform, a ratio between a pulse frequency of terahertz pulses generated by the second generating portion and a sampling frequency of the pulse-shaped probe light for taking terahertz pulses from the object into the detecting portion is preferably n:1 (where n is a natural number). Typically, the pulse frequency is equal to the sampling frequency. Further, timewidth of the terahertz pulse reaching the detecting portion is set longer than the sampling timewidth, and generation of the terahertz pulse and sampling for the detection are executed approximately simultaneously.

The following constructions within the scope of the above fundamental construction can also be used.

A photoconductive device of semiconductor, such as gallium arsenide, can be used, and the terahertz pulse can be generated by optically gating the device with the pulse-shaped pump light. The sampling can be achieved by optically gating the device with the pulse-shaped probe light. The terahertz pulse can also be generated by using other semiconductor crystals, negative resistance devices or semiconductor devices, such as a quantum cascade laser, resonance tunnel diode and Gunn diode, and electro-optic crystals.

As the optical pulse for optical gating, optical pulses at a differential frequency between two lasers of different laser wavelengths can be used In addition to the use of the photoconductive device, the optical sampling can also be executed by a sampling method using Pockels effect of the electro-optic effect, or by using thermo-detectors or the like, such as a bolometer. The gate timing on the generator side and the detector side can be performed by a method in which pump light and probe light for gating are generated by division of pulse-shaped light. Other methods can also be used so long as approximately simultaneous gating can be executed on both generator and detector sides.

A transmitting portion for transmission of the terahertz pulse can be transmission lines such as a strip-line transmission path, as well as a spatial portion described below. In the case of the transmission line, the object can be placed thereon.

The delay portion can be arranged not only in a path of the probe light, but also in a path of the pump light. To generate and change a relative delay between the probe light and the pump light, the delay portion typically only needs to be placed in at least one of the above light paths. Further, any means can be used so long as it can change the relative timing between optical gatings executed on the both sides. Thus, the detection time of the field intensity can be appropriately adjusted.

Preferred embodiments of the present invention will be hereinafter described with reference to the drawings.

FIG. 1 illustrates an example embodiment of the present invention. In FIG. 1, laser light 2 emitted from a laser portion 1 is divided into two beams, and these are respectively guided to a generating portion 3 and a first delay portion 8. In the generating portion 3, terahertz pulses 4 are generated by incidence of pump light of the laser light 2 thereon. The terahertz pulse 4 is directed to an object 5. Terahertz pulses 50 from the object 5 are guided to a detecting portion 6. The terahertz pulse 50 and probe light of the laser light 2 are guided to the detecting portion 6. When the laser light 2 is incident on the detecting portion 6, an instantaneous value of field intensity of the terahertz pulse 50 is detected by the detecting portion 6.

A fixed-point adjusting portion 7 supplies an adjustment amount for adjusting the optical path of probe light of the laser light 2, so that the detecting portion 6 can detect a first field intensity signal of a fixed point on the time domain waveform of the terahertz pulse 50 in a synchronous manner. The fixed point is, for example, a point of a peak value. The first delay portion 8 adjusts the optical path of probe light of the laser light 2 according to the optical path adjustment amount supplied from the fixed-point adjusting portion 7. Thus, a relative delay time (optical path difference) between pump light and probe light is adjusted.

A second delay portion 9 further adjusts the optical path of a portion of the laser light 2, whose optical path is adjusted by the first delay portion 8, so that the detecting portion 6 can detect a second field intensity signal of at least a point on the time domain waveform of the terahertz pulse 50. A time domain waveform scan controller 32 controls the second delay portion 9 so that the optical path of the laser light 2 adjusted by the second delay portion 9 can be successively changed. At least a portion of the time domain waveform of the terahertz pulse 50 is accordingly scanned, and detected by the detecting portion 6. The second delay portion 9 only needs to adjust the relative optical path difference in addition to the above relative optical path difference adjusted by the first delay portion 8. Therefore, the first delay portion 8 can be arranged at a place indicated by the dotted line in FIG. 1.

Figure 17:
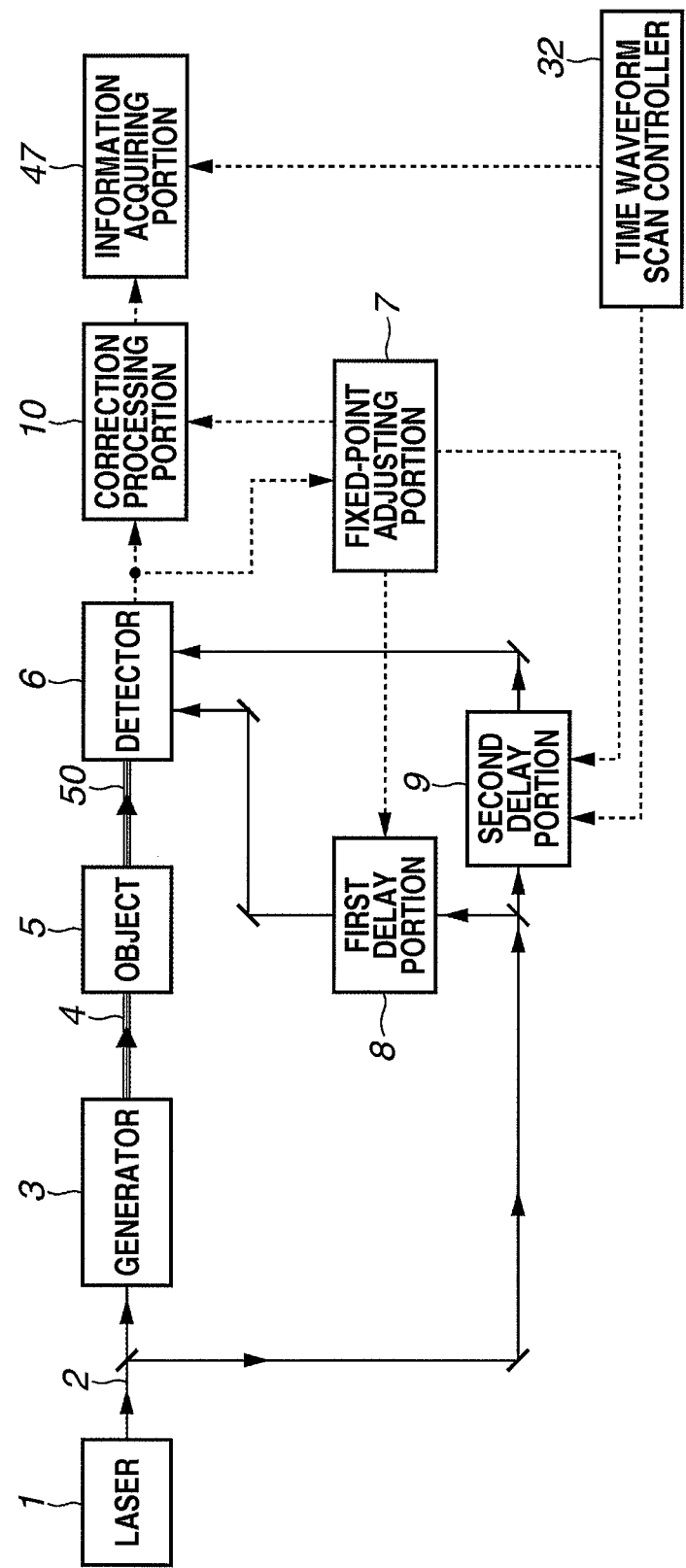
FIG. 17 is a view illustrating an example embodiment of an information acquiring apparatus and method according to the present invention.

In this case, the apparatus is constructed as illustrated in FIG. 17. The second delay portion 9 successively changes the optical path of probe light of the laser light 2 according to a sum of optical path adjustment amounts respectively supplied from the time domain waveform scan controller 32 and the fixed-point adjusting portion 7.

A correction processing portion 10 performs correction processing of the above second field intensity signal by using the first field intensity signal, or the optical path adjustment amount given to the laser light 2 by the first delay portion 8. An information acquiring portion 47 arranges second field intensity signals corrected by the correction processing portion 10 according to a change of the optical path of the laser light 2 adjusted by the second delay portion 9 that is successively controlled by the time domain waveform scan controller 32. Thus, at least a portion of the time domain waveform of the terahertz pulse 50 from the object 5 is regenerated. The time domain waveform can be Fourier-transformed, and analysis of, for example, component or particle size of the object 5 can be executed using the thus-obtained spectral information.

Figure 2:
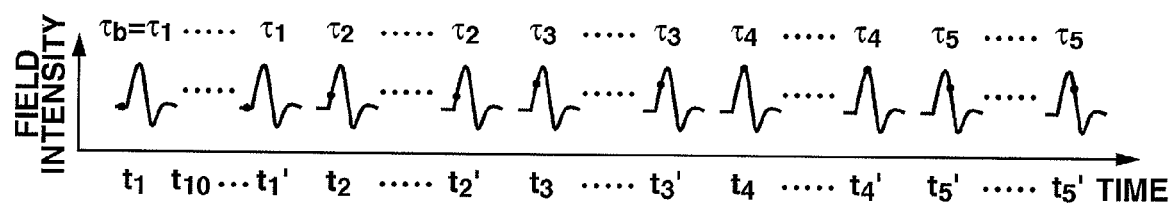
FIG. 2 is a view illustrating an example of a series of terahertz pulses, and incidence times of laser light for detecting the terahertz pulse.

A method of measuring the time domain waveform of the terahertz pulse 50 will be described with reference to FIG. 2. FIG. 2 is a graph in which the ordinate represents field intensity of the terahertz pulse 50 reaching the detecting portion 6, and the abscissa represents time. In FIG. 2, a black circle on the waveform of the terahertz pulse 50 indicates irradiation time of the detecting portion 6 with the laser light 2. At the irradiation time, an instantaneous field intensity of the terahertz pulse 50 is detected. A letter $\tau_b$ indicates delay time given to the laser light 2 by the second delay portion 9. The delay time corresponds to the optical path adjustment amount in terms of time.

Figure 3:
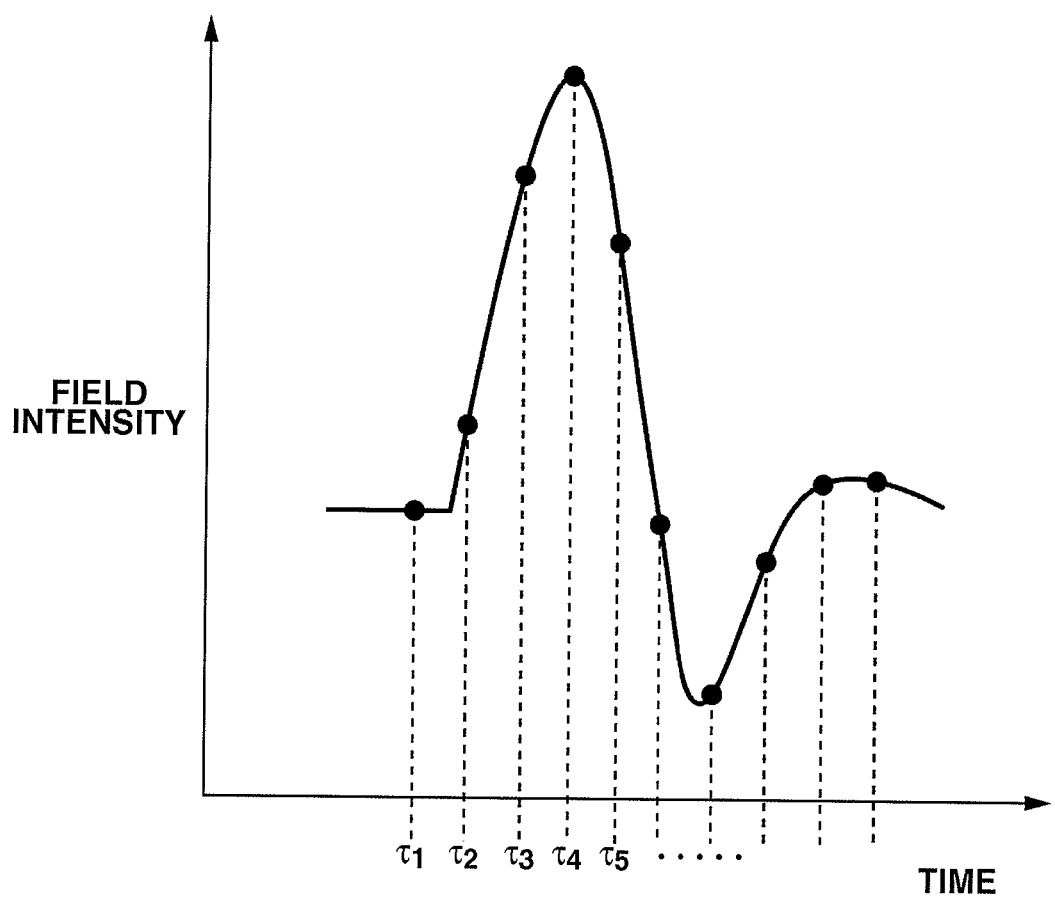
FIG. 3 is a view illustrating an example of the time domain waveform of a regenerated terahertz pulse.

When $\tau_b$ is fixedly set, for example, at $\tau_1$, the laser light 2 can be continuously applied to the terahertz pulse 50 at the same timing since repetitive frequencies of laser light 2 and terahertz pulse 50 are equal to each other. In other words, the same point on the terahertz pulse 50 can be continuously measured. In FIG. 2, $\tau_b$ is fixed from time $t_1$ to time $t_1'$, signals of repeating terahertz pulses 50 are summed during this timewidth and detected. When $\tau_b$ is changed from $\tau_1$ to $\tau_2$, another point on the terahertz pulse 50 can be measured. When the above measurement and the change of the delay time $\tau_b$ are repeated, the entire time domain waveform of the terahertz pulse 50 can be scanned. Thus, the time domain waveform of the terahertz pulse 50 can be regenerated as illustrated in FIG. 3 by arranging those measured values along the abscissa of delay time $\tau_b$ in a time-series manner.

Figure 4:
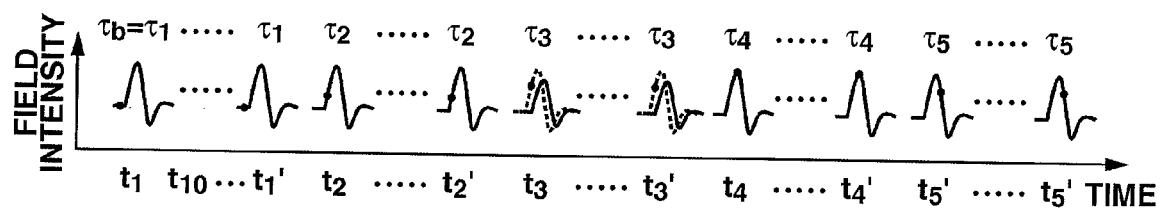
FIG. 4 is a view illustrating an example of a series of terahertz pulses, and incidence times of laser light for detecting the terahertz pulse where the thickness of an object temporarily increases.
Figure 5:
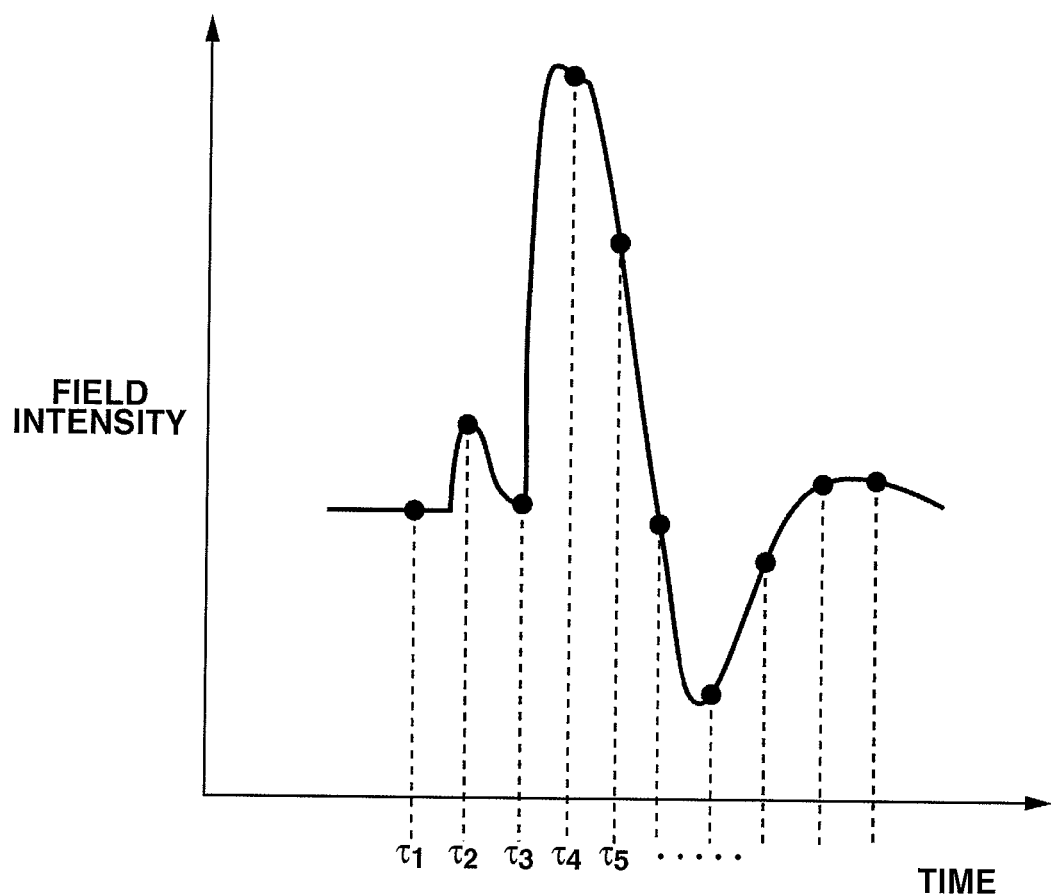
FIG. 5 is a view illustrating an example of the time domain waveform of a regenerated terahertz pulse where the thickness of an object temporarily increases.

Description will be made of influence of a change in thickness or density of the object 5 occurring when the correction processing portion 10 is omitted, with reference to FIG. 4. FIG. 4 schematically illustrates the field intensity of the terahertz pulse 50 reaching the detecting portion 6 when the thickness of the object 5 temporarily increases during an interval from time $t_3$ to time $t_3'$. The abscissa represents time. An increase in thickness or density of the object 5 normally causes delay in time at which the terahertz pulse 50 reaches the detecting portion 6, and a decrease in the field intensity. Accordingly, the time domain waveform of the terahertz pulse 50 changes from a shape indicated by the dotted line to a shape indicated by the solid line. In contrast, time, at which the laser light 2 reaches the detecting portion 6, remains unchanged since neither the fixed-point adjusting portion 7 nor the first delay portion 8 are provided. Hence, the time domain waveform of the terahertz pulse 50 obtained in this case becomes as illustrated in FIG. 5.

A method of correcting the waveform illustrated in FIG. 5 by reducing or compensating for influence of a change in thickness or density of the object 5 will be described with reference to FIGS. 6A and 6B.

First, in order to compensate for the delay in the reaching time of the terahertz pulse 50 due to an increase in thickness or density of the object 5, the detecting portion 6 follows at least a fixed point (for example, a point of a peak value) on the time domain waveform of the terahertz pulse 50, and detects a first field intensity signal thereof. An algorithm of following the peak point can be a method of hill-climbing search, for example. In the hill-climbing search, delay time is minutely changed around a certain point on the time domain waveform, and inclination of the field intensity relative to the change of delay time is calculated. A peak point exists on the right side of that certain point when the inclination is positive, while on the left side of that certain point when the inclination is negative. According to a value of the inclination, the delay time is changed so that that certain point approaches the peak point. This search is continued, and that point is brought to a point at which the inclination passes a zero point.

Figure 6A:
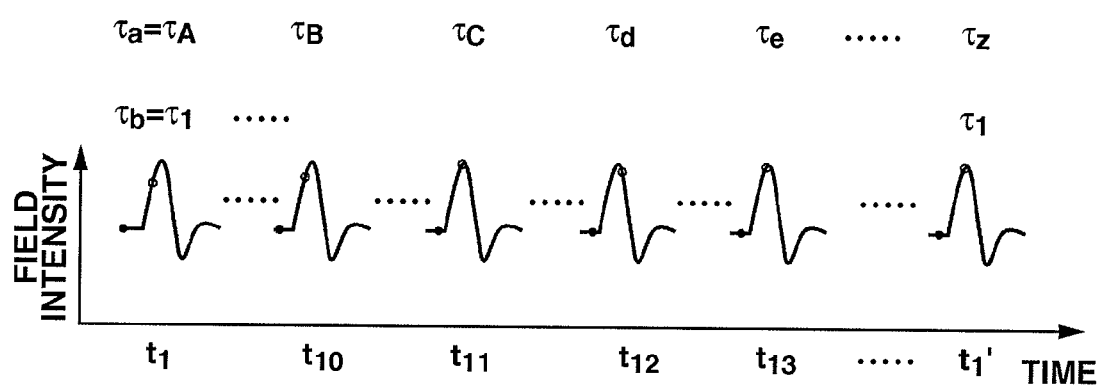
FIG. 6A is a view illustrating a portion of FIG. 2 enlarged with respect to an axis of time.
Figure 6B:
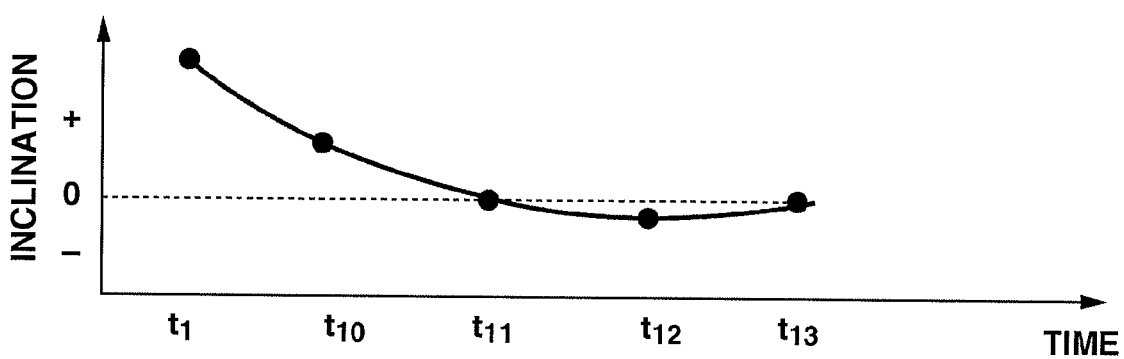
FIG. 6B is a view illustrating an example of a change in inclination at times at which irradiation of laser light for detecting the time domain waveform is performed.

FIGS. 6A and 6B illustrate the method of searching the peak value. FIG. 6A illustrates a portion from time $t_1$ to time $t_1'$ of FIG. 2 in an enlarged manner. In FIG. 6A, a white circle indicates time at which the laser light 2 transmitted through the first delay portion 8 is applied to the detecting portion 6. This shows that the detecting portion 6 detects an instantaneous field intensity of the terahertz pulse 50 at this moment. A letter $\tau_a$ indicates the delay time given to the laser light 2 by the first delay portion 8. FIG. 6B illustrates a change in the inclination with time. When the above algorithm is used in the above manner, it is possible to follow and detect a point, such as a peak point, at which the inclination is zero.

On the other hand, a black circle indicates time at which the laser light 2 transmitted through the first and second delay portions 8 and 9 is applied to the detecting portion 6. The sum of these delay times changes since $\tau_a$ changes and $\tau_b$ remains unchanged. The black circle shows that the detecting portion 6 detects an instantaneous field intensity of the terahertz pulse 50 at the moment when the laser light 2, to which the changing delay time is given, is applied to the detecting portion 6.

Principles of the correction will now be described. The peak value attenuates according to the Lambert-Beer law represented by the following equation (1), as the thickness of the object 5 increases $$I/I_0 = \exp(-\alpha L) \qquad \text{Equation (1)}$$

$I_0$ is the intensity of light applied to the object 5, I is the intensity of light transmitted through the object 5, $\alpha$ is the absorption coefficient, and L is the optical path of the object 5

Where $I_{10}$ is the first field intensity signal (here, the peak value) of the terahertz pulse 50 detected by the detecting portion 6 when no change in thickness L of the object 5 exists, $I_{20}$ is the second field intensity signal under such condition, $I_1$ is the first field intensity signal (here, the peak value) of the terahertz pulse 50 detected by the detecting portion 6 when the thickness L of the object 5 changes by $\Delta L$, and $I_2$ is the second field intensity signal under such condition, the following equations (2) and (3) are derived from the Lambert-Beer law $$I_1/I_{10} = \exp(-\alpha \Delta L) \qquad \text{Equation (2)}$$

$$I_2/I_{20} = \exp(-\alpha \Delta L) \qquad \text{Equation (3)}$$

Then, the following equation (4) is derived from the equations (2) and (3)

$$I_{20} = I_2 I_{10}/I_1 \qquad \text{Equation (4)}$$

$I_{10}$ is measured beforehand, or set at a predetermined value. Accordingly, $I_{20}$ can be obtained from $I_1$ and $I_2$ based on the equation (4). When those measured values containing correction values are arranged along the time axis of the delay time $\tau_b$ given by the second delay portion 9, the corrected time domain waveform of the terahertz pulse 50 can be regenerated When the density of the object changes with time, correction processing similar to the above can be performed on the assumption that the absorption coefficient $\alpha$ changes.

Figure 7:
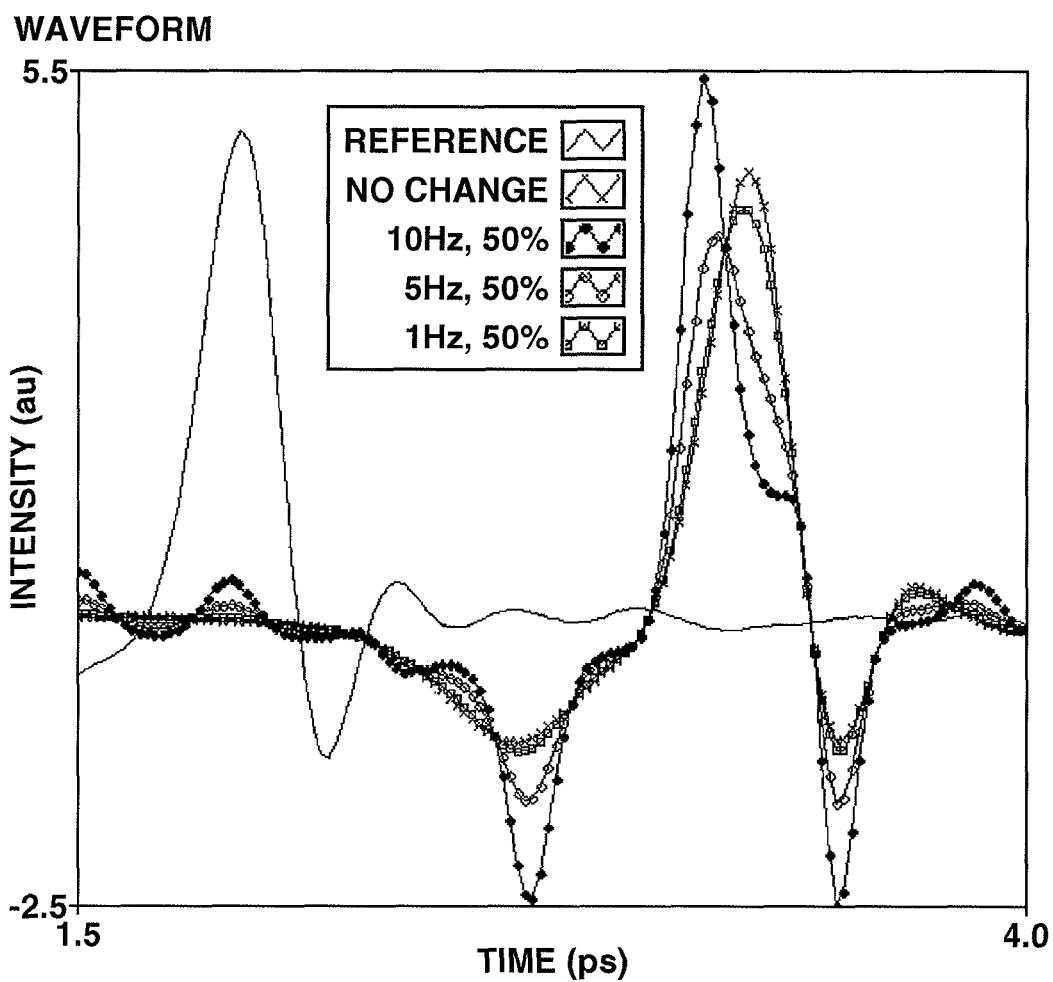
FIG. 7 is a view illustrating an example of the time domain waveform of a regenerated terahertz pulse.

Technical advantage of reduction of the influence due to a change in thickness or density of the object 5 will be described with reference to FIGS. 7 and 8. Any change can be represented by superimposition of sinusoidal waves according to the Fourier series expansion. Description will be made of a case where the change contains components of sinusoidal waves with several frequencies. For the convenience of simplicity, time delay in following the peak value is not considered. In FIG. 7, "REFERENCE" indicates the waveform regenerated when the object 5 is absent, and "NO CHANGE" indicates the waveform of the terahertz pulse 50 from the object 5 regenerated when neither thickness nor density vary.

Indications of "10 Hz, 50%", "5 Hz, 50%", and "1 Hz, 50%" respectively represent waveforms of the terahertz pulse 50 from the object 5 regenerated when thickness or density varies at frequencies of 10 Hz, 5 Hz and 1 Hz with variation of the amplitude of 50 percent. Here, for example, the change in thickness or density at the frequency of 5 Hz is superimposed on the time domain waveform of the terahertz pulse 50 with a period of 0.4 picosecond. It can be confirmed that shift of the peak position, change in the peak value and split of the peak appear in the regenerated time domain waveform of the terahertz pulse 50 due to the superimposition of the change in thickness or density.

Figure 8:
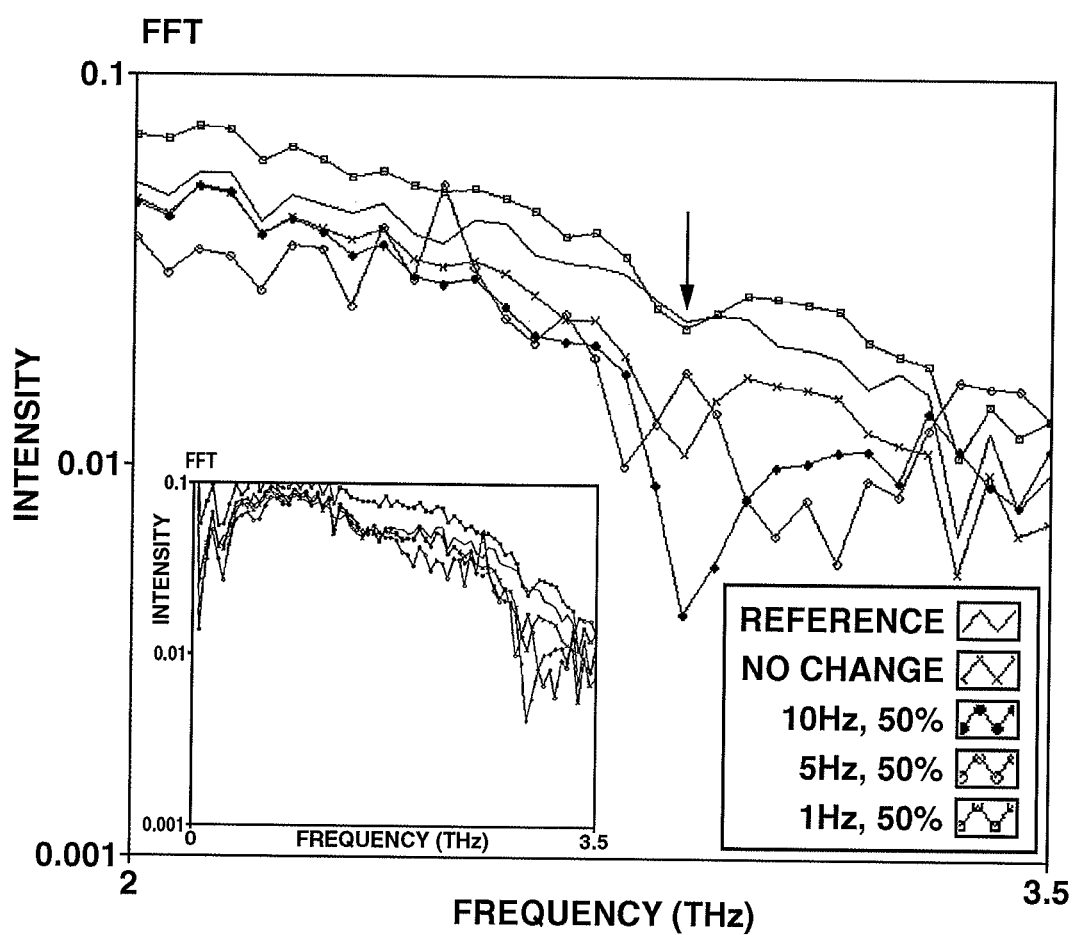
FIG. 8 is a view illustrating an example of a spectrum of the time domain waveform of the regenerated terahertz pulse illustrated in FIG. 7.

FIG. 8 illustrates spectra obtained by FFT (fast Fourier transform)-processing the time domain waveforms of the terahertz pulse 50. When information of "REFERENCE" is compared with information of "NO CHANGE" in FIG. 8, it can be seen that an absorption band of the object 5 exists as indicated by the arrow. Identification of component contained in the object 5 can be achieved based on the absorption band. However, no absorption band can be confirmed at the location pointed by the arrow in data of "5 Hz, 50%" and "1 Hz, 50%" in FIG. 8. Therefore, any component of the object 5 cannot be identified. In data of "10 Hz, 50%", a degree of fall at the absorption band is too large. Accordingly, precision in identification of a ratio of components decreases.

A case will be considered where the component, i.e., neither thickness nor density, of the object 5 varies while one time domain waveform of the terahertz pulse 50 is regenerated. In this case, a change in time delay or intensity of the terahertz pulse 50 due to the variation of the component can be compensated for as described above, similarly to a change in thickness or density. However, distortion of the terahertz pulse 50 due to variation of the component cannot be corrected, and a signal-to-noise ratio of measurement decreases in this case.

For the reason described above, with respect to a change in condition of the object 5 during regeneration of one time domain waveform of the terahertz pulse 50, technical advantage of the present invention for compensating for the influence of a change in thickness or density is notably large, while that for compensating for the influence of a change of component is relatively small.

According to this embodiment, it is possible to compensate for a change in thickness or density of the object 5, and measure the terahertz pulse 50 with reduced influence of a change in thickness or density of the object 5. Thereby, pseudo-component of the spectrum can be reduced, and measurement of component of the object 5 can be precisely achieved. For example, in measuring powder or liquid in a transport tube described below, or measuring an object in an in-process manner, thickness of the object varies with time. When this embodiment is used in such a case, unfavorable influence of such variation can be reduced, leading to improvement of analytic precision of the object.

More specific embodiments will now be described with reference to the drawings.

Figure 9:
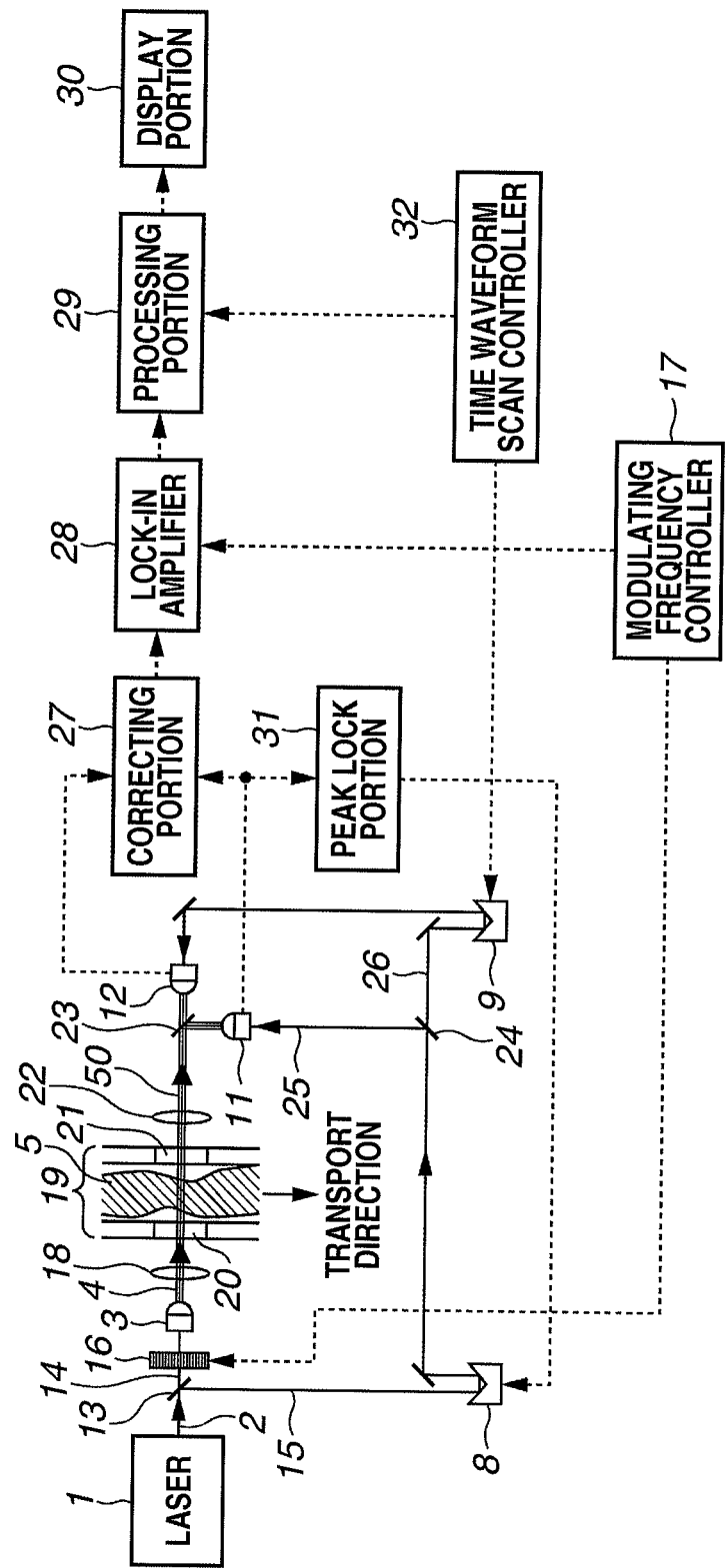
FIG. 9 is a view illustrating an example embodiment of an information acquiring apparatus and method.

FIG. 9 illustrates an example embodiment of an information acquiring apparatus and method according to the present invention, in which the above-described detecting portion 6 includes plural detectors.

In FIG. 9, a laser portion 1 emits laser light 2. A light source of a femtosecond pulse laser can be preferably used in the laser portion 1. Typically, wavelength of the laser light 2 is 780 nm, pulse width is in a range between several tens femtoseconds and several hundred femtoseconds, repetitive frequency is several tens MHz (for example, 76 MHz). The laser light 2 is split into laser light (pump light) 14 for generation and laser light (pump light) 15 for detection by a beam splitter 13.

Figure 10:
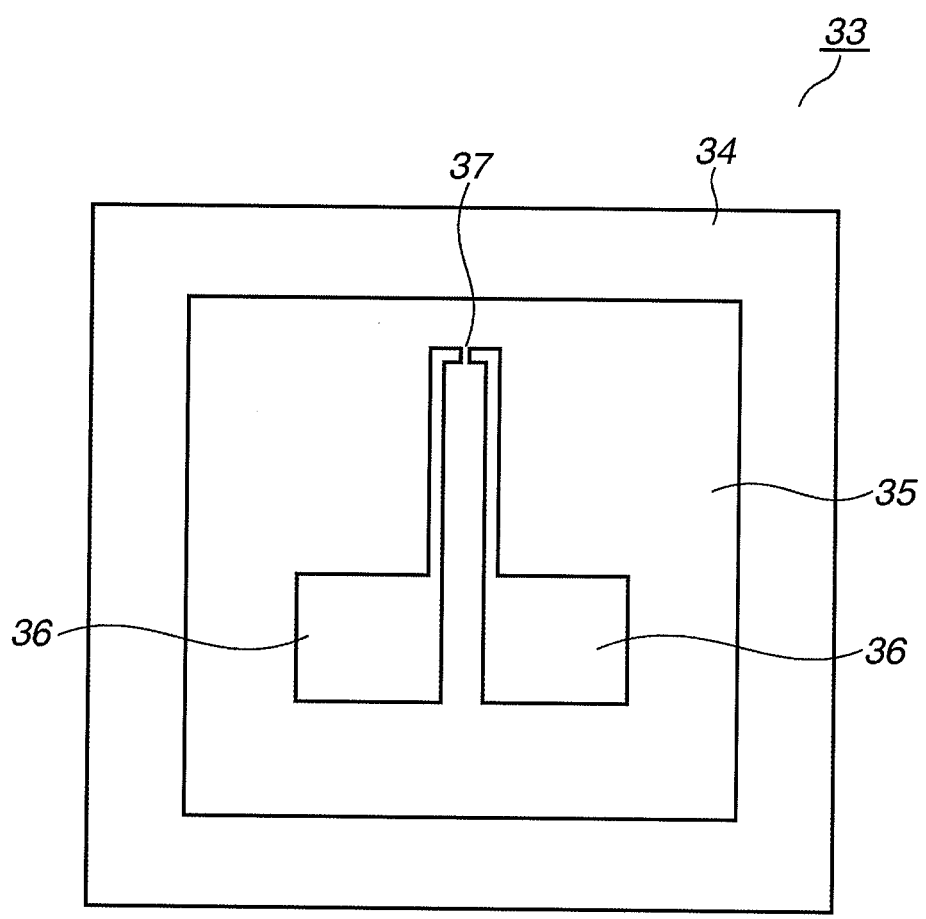
FIG. 10 is a view illustrating an example of a photoconductive device.

A photoconductive device is disposed in a generating portion 3. FIG. 10 illustrates a schematic structure of a preferable photoconductive device 33. In the photoconductive device 33, electrodes 36 of metal are deposited on a thin film 35 of gallium arsenide formed on a substrate 34. A gap 37 is formed between the electrodes 36. Width of the gap 37 is, for example, 5 microns. The substrate 34 can be formed of silicon. Thickness of the gallium arsenide film 35 is, for example, several microns.

Bias voltage is applied between the electrodes 36. Hence, upon irradiation of the gap 37 with the laser light 14 for generation, terahertz pulses 4 are produced. Typically, pulse width of the terahertz pulse 4 is in a range between several tens femtoseconds and several picoseconds, and repetitive frequency is several tens MHz, which is equal to that of the laser light 14 for generation. Since the intensity of the laser light 14 for generation is modulated by a chopper 16, the intensity of terahertz pulses 4 is similarly modulated. A device disposed in the generating portion 3 can be any device that can produce terahertz pulses 4 by the aid of the laser light 14 for generation. For example, DSAT (4-dimethylamino-N-methyl-4-stilbazolium Tosylate) crystal can also be used.

A modulating frequency controller 17 controls the chopper 16 so that the laser light 14 for generation is intensity-modulated at a modulating frequency of, for example, 1 kHz. A signal at the modulating frequency is also supplied to a lock-in amplifier 28. In this embodiment, the chopper 16 modulates the laser light 14 for generation. With respect to the modulating method, it is also adoptable to modulate the voltage applied across the gap 37 on the photoconductive device 33 provided in the generating portion 3.

Terahertz pulses 4 produced by the generating portion 3 are directed into a transport tube 19 through a window 20 thereof by a lens 18. In the transport tube 19, an object 5 (for example, medicine) under powdery or liquid condition flows in a transport direction indicated by the arrow in FIG. 9. The terahertz pulse 4 is transmitted through the object 5. The thus-transmitted terahertz pulse 50 emerges from the transport tube 19 through another window 21. The emerging terahertz pulse 50 passes through a lens 22, and is split into two by a beam splitter 23. One is directed to a first detecting portion 11, and the other is directed to a second detecting portion 12.

The laser light 15 for detection is transmitted through the first delay portion 8, and split into laser light (first probe light) 25 for first detection and laser light (second probe light) 26 for second detection by a beam splitter 24. The laser light 25 for first detection is directed to the first detecting portion 11. The laser light 26 for second detection passes the second delay portion 9, and is directed to the second detecting portion 12.

The first delay portion 8 changes the optical path of the laser light 15 for detection transmitted therethrough to simultaneously control delay times at which the laser light 25 for first detection and the laser light 26 for second detection respectively reach the first and second detecting portions 11 and 12. The second delay portion 9 changes the optical path of the laser light 26 for second detection transmitted therethrough to further control delay time at which the laser light 26 for second detection reaches the second detecting portion 12. For example, a structure with a retro-reflector placed on an automatic stage can be used as the delay portion 8 or 9.

The photoconductive device 33 as illustrated in FIG. 10 is arranged in each of the first detecting portion 11 and the second detecting portion 12. The first detecting portion 11 measures field intensity of the terahertz pulse 50 in the following manner. The second detecting portion 12 similarly measures the field intensity.

Figure 11A:
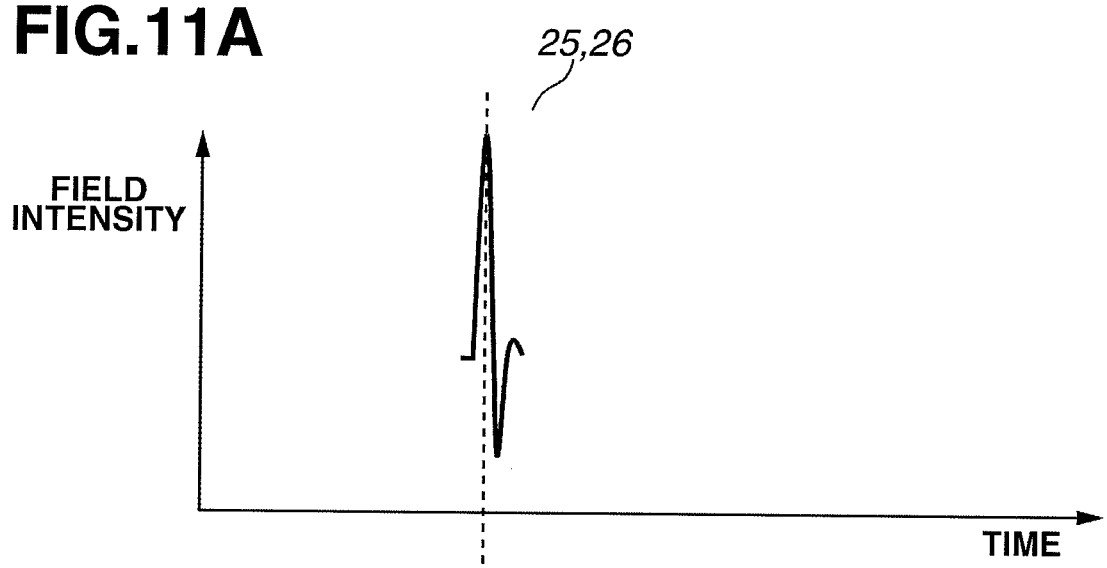
FIG. 11A is a view illustrating an example of incidence time of laser light for detecting a terahertz pulse.
Figure 11B:
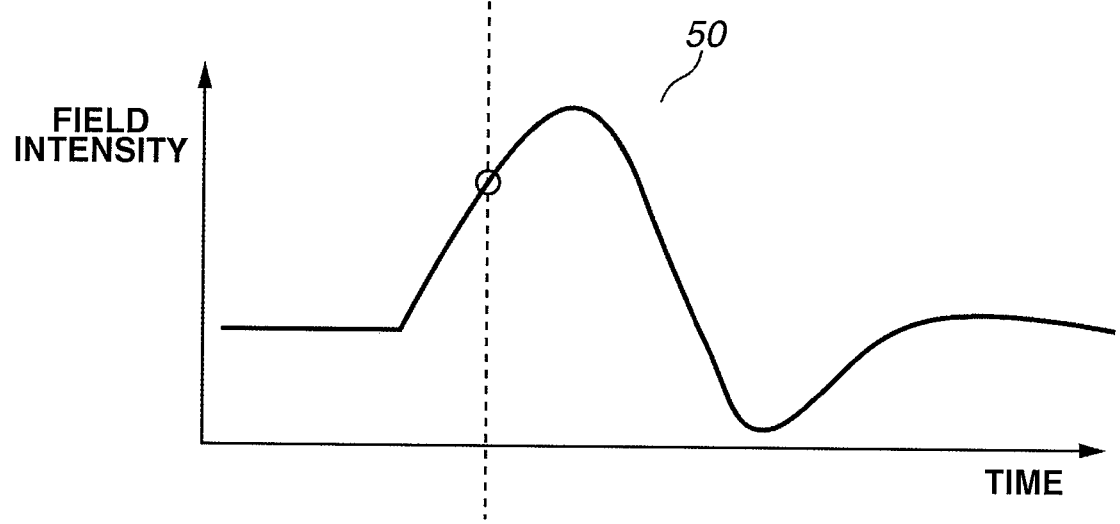
FIG. 11B is a view illustrating an example of the terahertz pulse incident on a detecting portion.

Terahertz pulse 50 from the object 5 and laser light 25 for first detection are applied to the gap 37 of the photoconductive device 33 in the first detecting portion 11. FIGS. 11A and 11B illustrate the relationship between those incidence times. Pulse width of the terahertz pulse 50 is larger than pulse width of the laser light 25 for first detection. Field intensity of the terahertz pulse 50 is detected as follows. Upon incidence of the laser light 25 for first detection on the gap 37 of the photoconductive device 33, carriers are generated in the gallium arsenide 35 present around the gap 37. When the terahertz pulse 50 is applied to the above location, carriers are accelerated by the electric field of the terahertz pulse 50 and reach the electrodes 36.

Thus, current flows between the electrodes 36 according to the field intensity of the terahertz pulse 50. Field intensity of the terahertz pulse 50 can be measured by measuring the current. Since current flows at the moment carriers exist, it is possible to measure the field intensity of a portion of the terahertz pulse 50 indicated by the white circle in FIG. 11B. Time resolution of the measurement increases as pulse width of the laser light 25 for first detection and life time of the carrier decrease.

The first detecting portion 11 follows and detects the peak value on the time domain waveform of the terahertz pulse 50. In contrast thereto, the second detecting portion 12 acquires the entire time domain waveform of the terahertz pulse 50.

A correcting portion 27 in the correction processing portion performs correction similar to the correction that is executed by the correction processing portion 10 in the above embodiment. Corrected second field intensity signal is supplied to a lock-in amplifier 28. The lock-in amplifier 28 extracts a component at a frequency equal to the modulating frequency, which the chopper 16 gives the laser light 14 for generation, from the signal supplied from the correcting portion 27. Typically, lock-in time constant and sampling time of the lock-in amplifier 28 are set at 30 ms, 0.1 seconds, respectively. When data is obtained at 1000 points, measuring time becomes 100 seconds. In this case, a change in thickness or density of the object 5 appearing with time scale below 100 seconds is superimposed on the time domain waveform of the terahertz pulse 50 detected by the detecting portion, and the analytic precision of condition, such as component or particle size, of the object 5 decreases.

Figure 12:
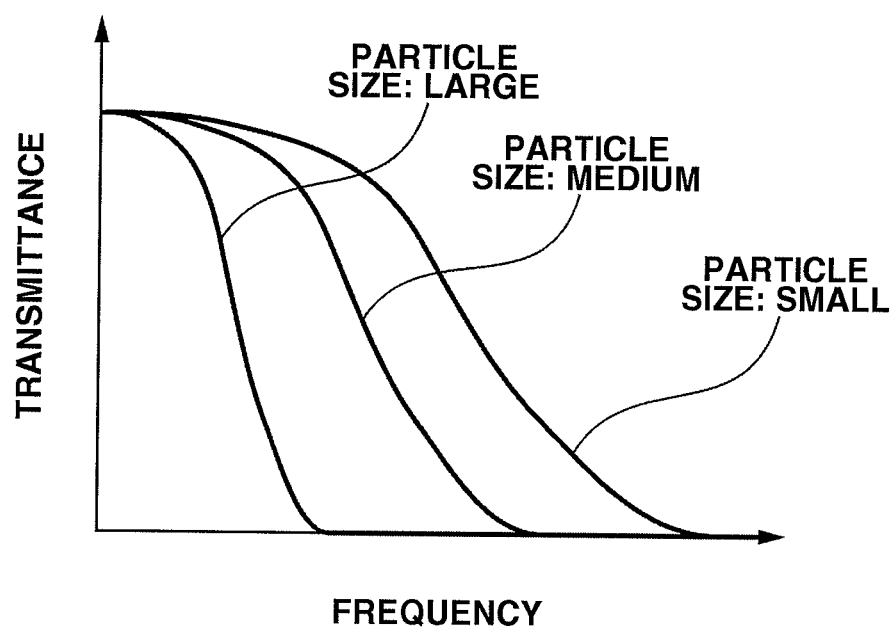
FIG. 12 is a view illustrating an example of a difference in transmittance spectrum due to a difference in the particle size of an object.

Output signal of the lock-in amplifier 28 and information of the delay time for scanning the time domain waveform are supplied to a processing portion 29. In the processing portion 29, output signals of the lock-in amplifier 28 are arranged in a time series manner based on the delay time supplied from a time domain waveform scan controller 32, and the terahertz pulse 50 is regenerated. Resolution of the time domain waveform of the regenerated terahertz pulse 50 is typically 20 femtoseconds. The time domain waveform of the terahertz pulse 50 can be Fourier-transformed to obtain its spectrum. Component of the object 5 can be identified using the spectrum. Particle size of the object 5 can also be identified using the spectrum. Depending on the particle size of substance of the object 5, the cutoff of the transmittance spectrum varies as illustrated in FIG. 12. Therefore, the particle size can be recognized from the spectrum. Cutoffs of particle sizes in a range between several microns and several thousand microns are in the terahertz region. The particle size can be measured using the apparatus of this embodiment.

Time domain waveform of the terahertz pulse 50, spectrum, and component or particle size can be supplied to a display portion 30, and displayed thereon.

A flowchart of measuring a waveform of the terahertz pulse 50 will be described with reference to FIG. 13.

In step S0, irradiation of the object 5 with terahertz pulses is started. In step S1, operation of the second delay portion 9 is paused.

From step S2 to step S9, peak lock operation is executed. In step S2, the first detecting portion 11 detects field intensity of the terahertz pulse 50 at a certain delay time. In step S3, the first delay portion 8 minutely changes the optical path. The amount of such minute change is, for example, about 50 microns. After the change in the optical path, the first detecting portion 11 detects field intensity of the terahertz pulse 50 (step S4). In step S5, the peak lock portion 31 calculates the inclination from two field intensities detected in steps S2 and S4, and the change amount of the optical path changed in step S3. The peak lock portion 31 corresponds to the fixed-point adjusting portion 7 in FIG. 1.

In step S6, if the inclination obtained by the peak lock portion 31 passes zero or not is judged. If the zero-crossing takes place, the step proceeds to step S10. If no zero-crossing occurs, the step proceeds to step S7. In step S7, when the inclination is positive, the step proceeds to step S8, and the first delay portion 8 increases the optical path. When the inclination is negative, the step proceeds to step S9, and the first delay portion 8 decreases the optical path. Thus, the optical path is adjusted toward a direction approaching the peak. Although the change amount of the optical path is typically about 6 microns in the above operation, the change amount can be made larger when the inclination is large.

After this operation, the step returns to step S2. Here, the step can proceed to step S10 without returning to step S2 after step S8 or S9. Such operation can be selected when fast measuring speed is desired even if the measuring precision slightly lowers. It is desirable that the time constant of the peak lock operation is considerably shorter than the time constant of a change in thickness or density of the object 5. For example, when the latter time constant is 100 ms, the former time constant is preferably below a 10-ms order.

Now that the peak value comes nearby, detection of the field intensity of the terahertz pulse 50 by the second detecting portion 12 and correction thereof are performed in steps from step S10 to step S14. In step S10, a detection value acquired in step S4 is represented as $I_1$. In step S11, the second detecting portion 12 detects the field intensity of the terahertz pulse 50, and represents it as $I_2$. In step S12, the correcting portion 27 calculates $I_2/I_1$. By this calculation, influence of a change in thickness of the object 5 contained in $I_2$ can be removed. The calculated result is supplied to the lock-in amplifier 28, and phase detection is performed using the modulating frequency of the chopper 16 as a carrier frequency in step S13. Thereafter, if the pause interval of the second delay portion 9 is above 0.1 second or not is judged in step S14. The pause interval is an accumulation time at a point on the time domain waveform of the terahertz pulse 50. When the accumulation time has no yet reached above 0.1 seconds, the step is returned to step S2. When the accumulation time has reached above 0.1 seconds, the step proceeds to step S15.

In step S15, if scan over the entire time domain waveform of the terahertz pulse 50 is completed or not is judged. When not yet, the second delay portion 9 increases the optical path by one step in step 17, and the step is returned to step S2. When the scan is completed, the step proceeds to step S16.

Steps S16, S18 and S19 are steps in which the time domain waveform of the terahertz pulse 50 is regenerated and component of the object 5 is identified. In step S16, the processing portion 29 arranges signals from the lock-in amplifier 28 in a time series manner according to the delay time supplied from the time domain waveform scan controller 32, and regenerates the time domain waveform of the terahertz pulse 50. In step S18, the time domain waveform is FFT-processed in the processing portion 29, and the spectrum of the terahertz pulse 50 is calculated. In step S19, the spectrum is compared with a stored spectrum table in the processing portion 29, and component of the object 5 is identified. The spectrum table is, for example, a table of calibration curves using absorption bands of components contained in the object 5.

As described above, one waveform of the terahertz pulse 50 can be regenerated, and component of the object 5 can be identified. It is also possible to store and arrange peak values detected by the first detecting portion 11 in order to simultaneously measure changing conditions of thickness or density of the object 5.

Figure 13:
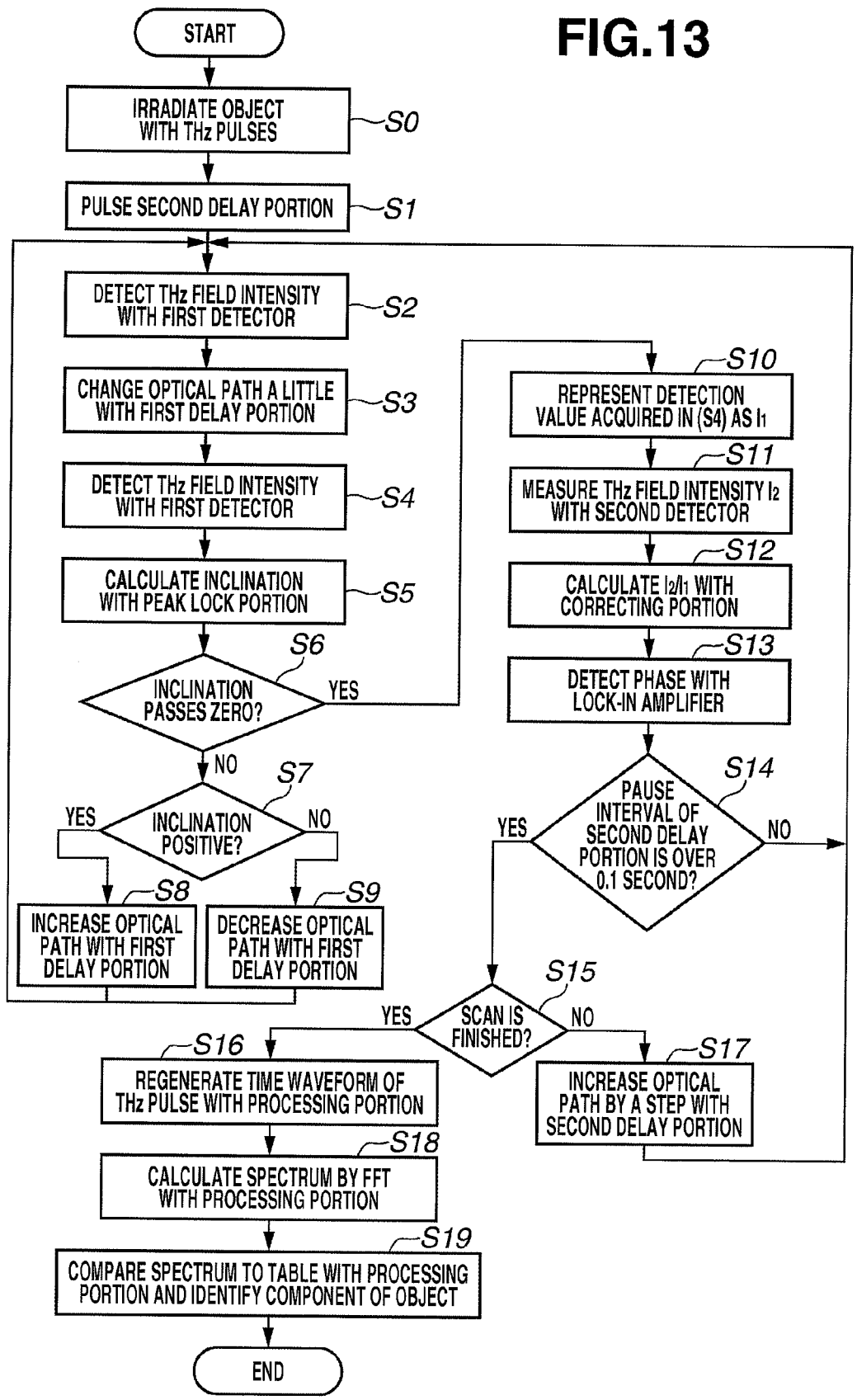
FIG. 13 is a view illustrating an example of a flowchart for measuring the time domain waveform of a terahertz pulse, and identifying the component of an object.

In the flowchart of FIG. 13, the peak lock operation from step S1 to step S9, and the detection in step S10 are alternately performed. However, the frequency of the peak lock operation can be reduced to a degree that can enable the following of a change in thickness or density of the object 5. The peak lock operation can be performed at intervals of 100 ms, for example. Further, the correction in step S12 can be collectively executed after the scan is finished in step S15.

Figure 18:
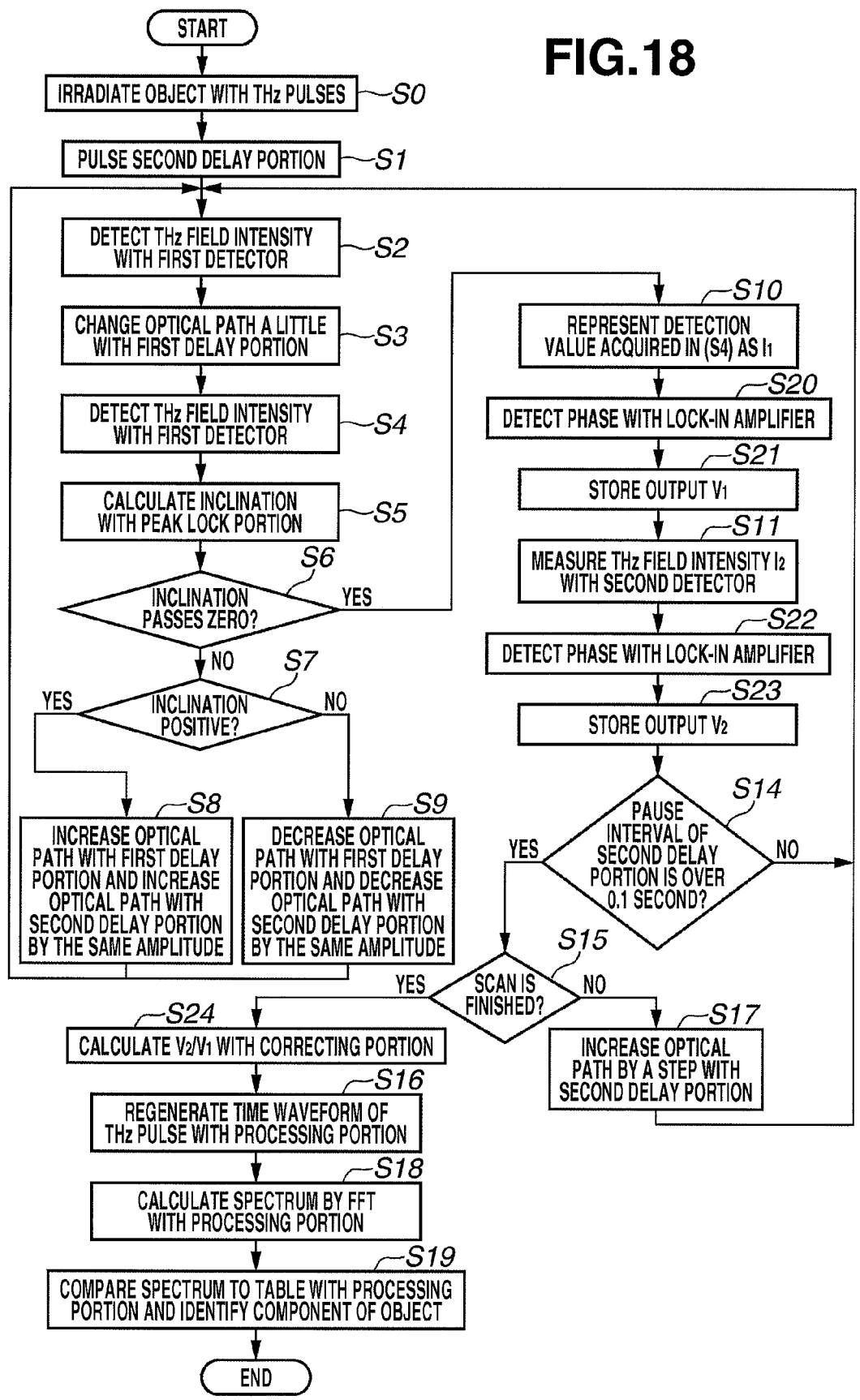
FIG. 18 is a view illustrating another example of a flowchart for measuring the time domain waveform of a terahertz pulse, and identifying the component of an object.

In the construction as illustrated in FIG. 17, such a flowchart as illustrated in FIG. 18 modified from that of FIG. 13 can be adopted. In the flowchart of FIG. 18, the second delay portion 9 successively changes the optical path of probe light of the laser light 2 according to a sum of optical path adjustment amounts respectively supplied from the time domain waveform scan controller 32 and the fixed-point adjusting portion 7. In steps S8 and S9, the change amount of the optical path in the second delay portion needs to be coincident with the change amount in the first delay portion.

In this embodiment, the construction is as follows. The light source includes the laser portion 1 adapted to emit pulse-shaped laser light which is divided to produce the pulse-shaped pump light, the first probe light and the second probe light. The first delay portion 8 adjusts the optical path of the first probe light 25, which is a portion of the laser light reaching the detecting portion for achieving the synchronization. The second delay portion 9 further adjusts the optical path of the second probe light 26 which is a portion of the first probe light whose optical path is adjusted by the first delay portion 8.

There are further provided the peak lock portion or the fixed-point adjusting portion 31 for supplying the signal of an adjustment amount of the optical path by which the first delay portion 8 performs the above adjustment, and the time domain waveform scan controller 32 for supplying the signal of an additional adjustment amount of the optical path by which the second delay portion 9 performs the above adjustment. The correction processing portion 27 compensates for the influence of a change in condition of the object on the time domain waveform obtained by the detecting portion, using the field intensity of the predetermined fixed point. The above change in condition occurs within a time shorter than a time during which the time domain waveform of the pulse 50 of terahertz radiation from the object 5 is acquired by the control of the second delay portion with the time domain waveform scan controller.

Further, the detecting portion includes a plurality of detectors. At least a detector 11 receives the first probe light transmitted through the first delay portion, and at least another detector 12 receives the second probe light transmitted through the first delay portion and the second delay portion.

According to the apparatuses and methods of this embodiment, influence of a change in condition, such as thickness or density, of the object 5 on the time domain waveform of terahertz pulse from the object can be compensated for. Accordingly, the above influence can be reduced in measuring the time domain waveform of terahertz pulse 50 from the object 5. Particularly, in this embodiment, plural detectors 11 and 12 are used, and first and second field intensity signals can be taken from different detectors. Therefore, measurement can be performed by a simple processing.

Figure 14:
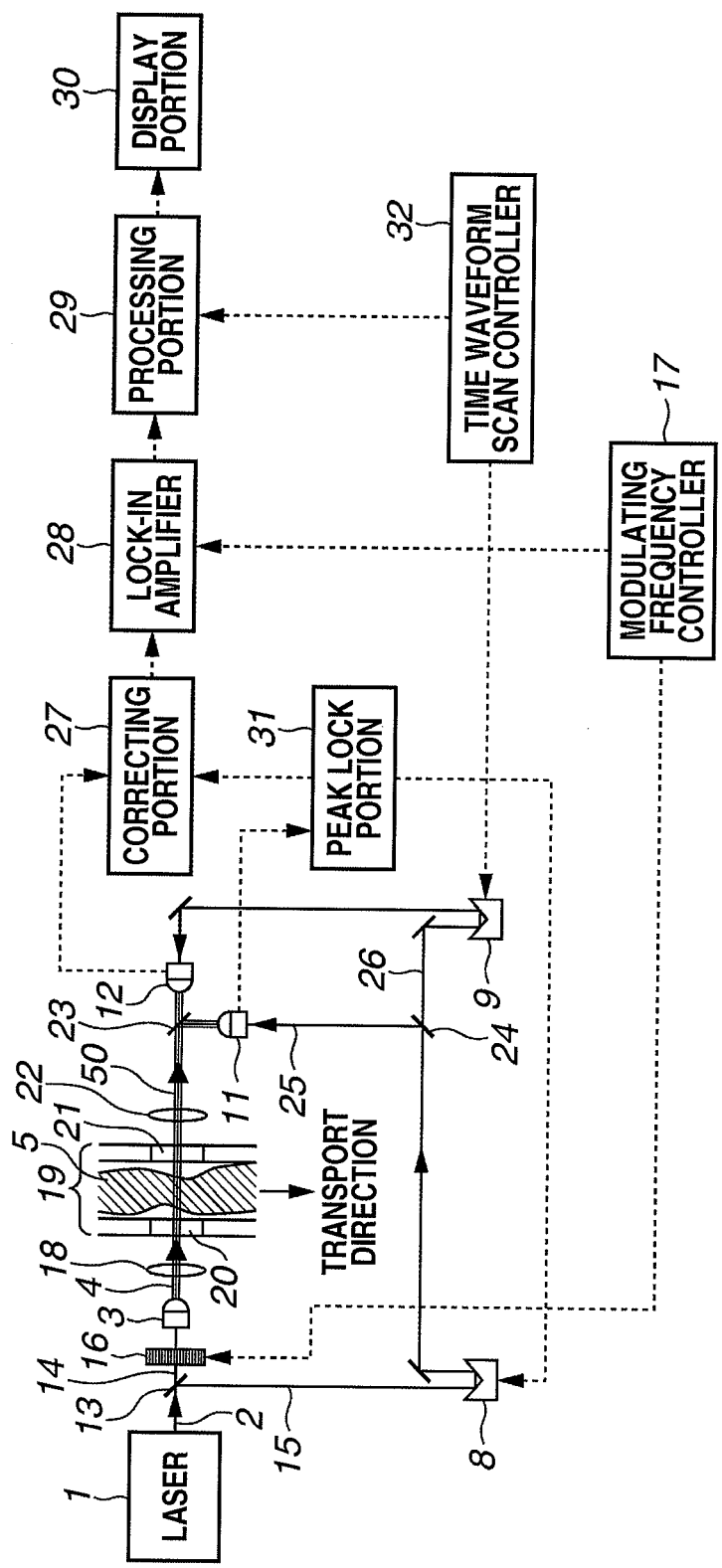
FIG. 14 is a view illustrating an example embodiment of an information acquiring apparatus and method.

Another example embodiment of an information acquiring apparatus and method will be described with reference to FIG. 14. In this embodiment, a value of the field intensity detected by the second detecting portion 12 is corrected using the delay time given to the laser light 15 for detection by the first delay portion 8. In other words, the correction processing portion corrects influence of a change in condition of the object on the time domain waveform, using the adjustment amount of the optical path by which the first delay portion performs the adjustment. Other portions of this embodiment are the same as those of the above-described embodiment. In FIG. 14, portions having the same functions as those illustrated in FIG. 9 are designated by like reference numerals.

In FIG. 14, a value measured by the first detecting portion 11 is supplied to the peak lock portion 31. In the peak lock portion 31, using the above-described peak lock method, the first delay portion 8 adjusts the delay time given to the laser light 15 for detection so that the first detecting portion 11 follows the peak value of the time domain waveform of the terahertz pulse 50. Information of this delay time is supplied to the correcting portion 24 from the peak lock portion 31.

Where $\tau_D$ is the delay time of the peak of the terahertz pulse 50 when the terahertz pulse 50 passes through the object 5 by a thickness $\Delta L$, c is the velocity of light in vacuum, and n is the index of refraction of the object 5, the following equation (5) is given.

$$\Delta L = c\tau_D/n \quad \text{Equation (5)}$$

The following relationship (6) can be derived from equation (5) and equation (1).

$$I_0 = I/\exp(-\alpha c\tau_D/n) \quad \text{Equation (6)}$$

where $I_0$ is the intensity of transmitting light when a change $\Delta L$ in thickness of the object 5 does not yet occur, and I is the intensity of transmitting light when the change $\Delta L$ in thickness of the object 5 occurs.

In the correcting portion 27 constructing the correction processing portion, a corrected measurement value $I_0$ is calculated based on equation (6). According to this embodiment, even when a change in the peak value is small, if the delay amount of the peak is large, measurement with high precision can be achieved using this delay amount of the peak. Other points of operation and technical advantage of this embodiment are the same as those in the above-described embodiment of FIG. 9.

Figure 15:
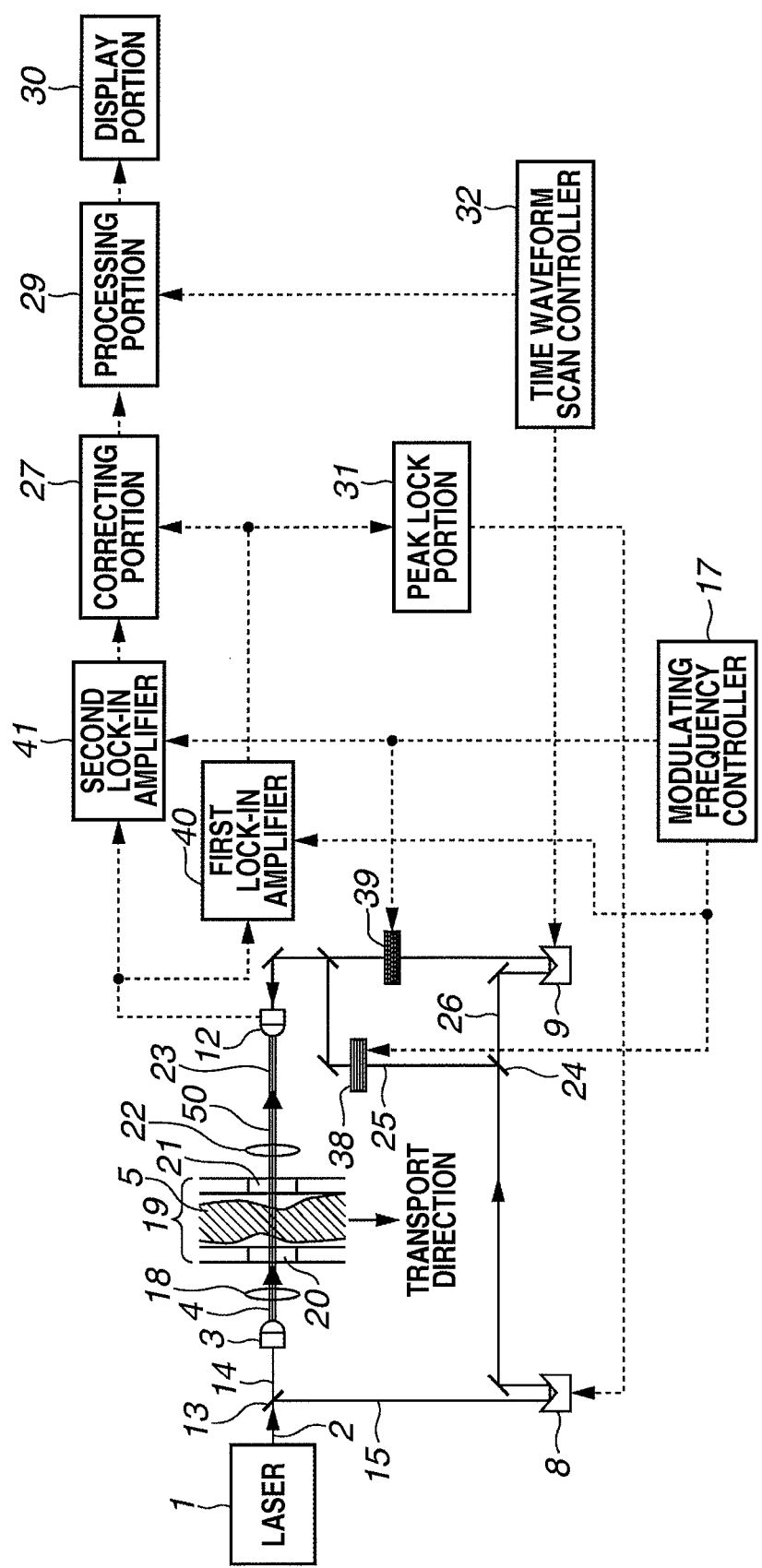
FIG. 15 is a view illustrating an example embodiment of an information acquiring apparatus and method.

Another example embodiment of an information acquiring apparatus and method will be described with reference to FIG. 15. In this embodiment, only a detector is provided in the detecting portion 6. Other portions of this embodiment are the same as those of the above-described embodiment of FIG. 9. In FIG. 15, portions having the same functions as those illustrated in FIG. 9 are designated by like reference numerals.

In FIG. 15, a first chopper 38 optically chops the laser light 25 for first detection, and a second chopper 39 optically chops the laser light 26 for second detection. Chopping frequencies of the first chopper 38 and the second chopper 39 are different from each other. For example, the chopping frequency of the first chopper 38 is 1 kHz, and the chopping frequency of the second chopper 39 is 1.7 kHz.

In this embodiment, a value measured by the detector 12 is supplied to both first lock-in amplifier 40 and second lock-in amplifier 41. Carrier frequency of the first lock-in amplifier 40 is coincident with the chopping frequency of the first chopper 38, and carrier frequency of the second lock-in amplifier 41 is coincident with the chopping frequency of the second chopper 39. Therefore, the first lock-in amplifier 40 can detect a measurement value induced by the laser light 25 for first detection. On the other hand, the second lock-in amplifier 41 can detect a measurement value induced by the laser light 26 for second detection. In other words, the detecting portion includes only a detector 12 for receiving the first probe light and the second probe light, and the first probe light and the second probe light are modulated in mutually different manners.

When time of irradiation of the detecting portion 12 with the laser light 25 for first detection always follows the peak value of the terahertz pulse 50, the signal output from the first lock-in amplifier 40 corresponds to the peak value of the terahertz pulse 50.

Output signal of the first lock-in amplifier 40 and output signal of the second lock-in amplifier 41 are corrected in the correcting portion 27 in the method described in the above-described embodiment. The output signal of the first lock-in amplifier 40 is also supplied to the peak lock portion 31.

According to this embodiment, since influence of a positional deviation between two detectors can be solved by the arrangement of a single detector, measurement with high precision can be achieved. Other points of operation and technical advantage of this embodiment are the same as those in the above-described embodiment of FIG. 9.

Figure 16:
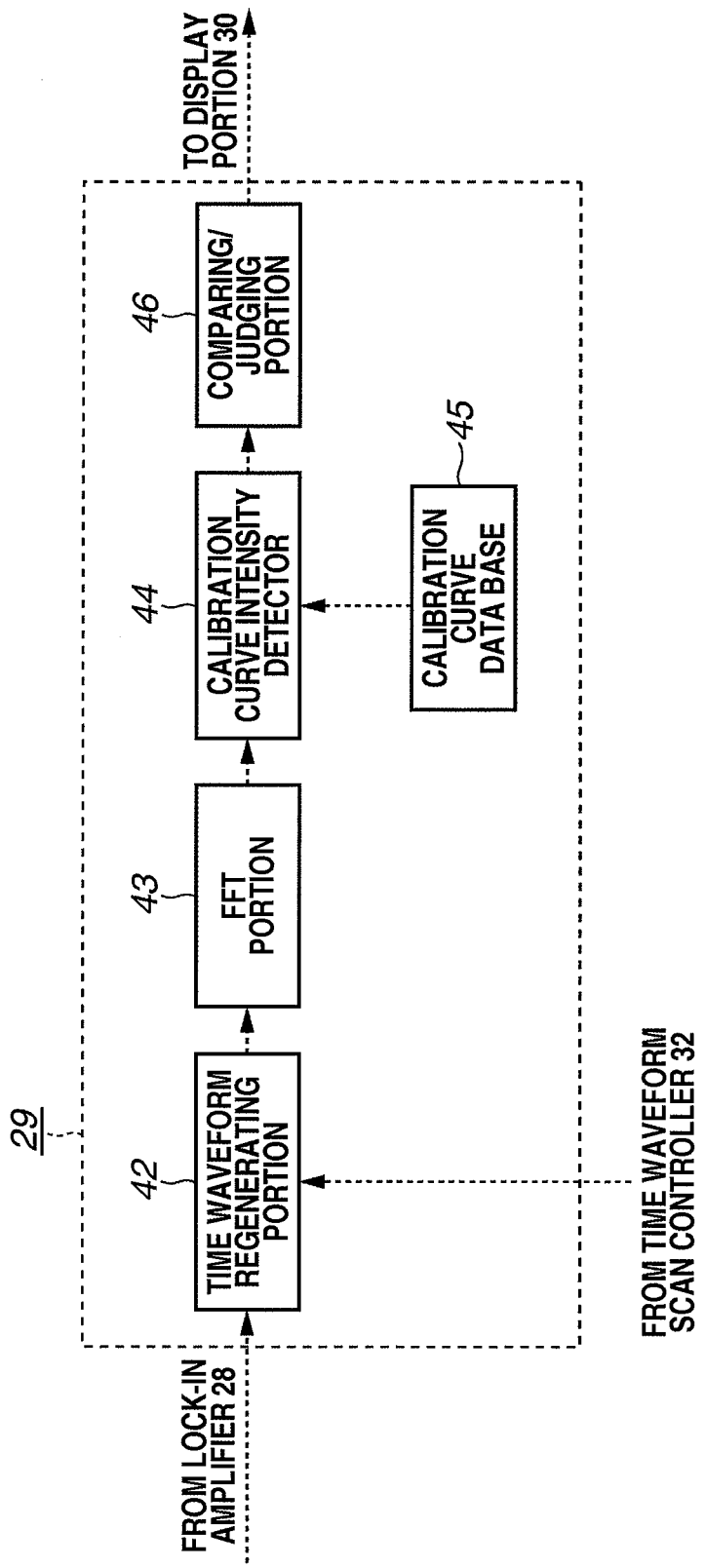
FIG. 16 is a view illustrating a processing portion in an embodiment of an information acquiring apparatus and method.

Yet another example embodiment of an information acquiring apparatus and method will be described with reference to FIG. 16. In this embodiment, based on the time domain waveform of the terahertz pulse corrected in the correction processing step, an abnormal value of characteristics, such as a change in component, of the object 5 is detected. FIG. 16 illustrates a processing portion 29 of this embodiment. Other portions of the information acquiring apparatus of this embodiment are the same as those in the above-described embodiment of FIG. 9.

FIG. 16, a signal of the lock-in amplifier 28 and information of delay time of the waveform scan controller 32 are supplied to a time domain waveform regenerating portion 42. In the time domain waveform regenerating portion 42, the time domain waveform of the terahertz pulse 50 is regenerated based on those two signals. An FFT portion 43 converts the regenerated time domain waveform into its spectrum by the fast Fourier transform. A calibration curve intensity detecting portion 44 extracts the spectral intensity at a wavelength designated by calibration curve data base 45. As the frequency designated by the calibration curve data base 45, absorption band at the time of a normal or abnormal condition of the object 5 can be used, for example.

In a comparing/judging portion 46, if the condition of the object 5 is normal or not is judged based on the spectral intensity obtained by the calibration curve intensity detecting portion 44. The judged result is displayed on the display portion 30. When the comparing/judging portion 46 judges the condition to be abnormal, treatment, such as pause of production of the object 5, can be executed, for example. A criterion of judging the object 5 to be under normal or abnormal condition is, for example, that a ratio between the intensity of absorption band at the time of the normal condition and the intensity of absorption band at the time of the abnormal condition is less or more than a given value.

According to this embodiment, when the abnormal condition of the object 5 is sensed, the sensed result can be displayed on the display portion 30, or production of the object 5 can be paused, for example. Thus, yield of the object 5 can be improved. Other points of operation and technical advantage of this embodiment are the same as those in the above-described embodiment of FIG. 9.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2008-024631, filed 2008 Feb. 5, and 2008-324791, filed 2008 Dec. 19, which are hereby incorporated by reference herein in their entirety.

What is claimed is:

1. An information acquiring method for acquiring information of an object by using terahertz time domain spectroscopy, the method comprising:
   a first generating step of generating pulse-shaped pump light, first probe light and second probe light in synchronization with each other;
   a second generating step of generating pulses of terahertz radiation by using the pump light;
   a detecting step of detecting pulses of terahertz radiation from an object irradiated with the pulses of terahertz radiation;
   a first delay step of adjusting an optical path difference between an optical path of the pump light used in the second generating step and an optical path of the first probe light used in the detecting step, so that a field intensity of a predetermined fixed point on a time domain waveform of the pulse of terahertz radiation from the object is detected in the detecting step, following the predetermined fixed point;
   a second delay step of adjusting an optical path difference between the optical path of the pump light used in the second generating step and an optical path of the second probe light used in the detecting step by a sum of an additional optical path adjustment amount and the optical path difference adjusted in the first delay step, so that the time domain waveform of the pulse of terahertz radiation from the object is obtained in the detecting step; and
   a correction processing step of compensating for influence of a change in condition of the object on the time domain waveform obtained in the detecting step by using the field intensity of the predetermined fixed point, or an adjustment amount of the optical path adjusted in the first delay step.

2. An information acquiring method according to claim 1, wherein the change in condition of the object is a change in thickness of the object, or a change in density of the object.

3. An information acquiring method according to claim 1, wherein a component or particle size of the object is recognized based on the time domain waveform of the pulse of terahertz radiation from the object corrected in the correction processing step.

* * * * *